United States Patent
Berg et al.

(10) Patent No.: US 6,505,066 B2
(45) Date of Patent: Jan. 7, 2003

(54) CATHETER HAVING A HIGH TENSILE STRENGTH BRAID WIRE CONSTRAINT AND METHOD OF MANUFACTURE

(75) Inventors: Todd A. Berg, Lino Lakes, MN (US); Jason A. Galdonik, Brooklyn Park, MN (US); Henry Pepin, Loretto, MN (US); Brian Scovil, New Hope, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 46 days.

(21) Appl. No.: 09/775,369

(22) Filed: Feb. 1, 2001

(65) Prior Publication Data

US 2001/0005552 A1 Jun. 28, 2001

Related U.S. Application Data

(63) Continuation of application No. 09/346,973, filed on Jul. 2, 1999, now Pat. No. 6,212,422, which is a continuation of application No. 08/936,983, filed on Sep. 25, 1997, now Pat. No. 5,954,651, which is a continuation-in-part of application No. 08/800,926, filed on Feb. 13, 1997, now Pat. No. 5,951,495, which is a continuation-in-part of application No. 08/441,260, filed on May 15, 1995, now Pat. No. 5,603,705, which is a continuation of application No. 08/171,925, filed on Dec. 22, 1993, now abandoned, application No. 09/775, 369, filed on Feb. 1, 2001, which is a continuation-in-part of application No. 08/489,001, filed on Jun. 8, 1995, now Pat. No. 5,674,208, which is a continuation of application No. 08/108,973, filed on Aug. 18, 1993, now abandoned.

(51) Int. Cl.$^7$ ................................................. A61B 5/00
(52) U.S. Cl. .......................................... 600/435; 156/149
(58) Field of Search .............................. 600/434, 435, 600/585; 604/282, 523, 529, 527; 156/158, 149

(56) References Cited

U.S. PATENT DOCUMENTS

| 3,416,531 A | 12/1968 | Edwards ..................... 128/348 |
| 3,485,234 A | 12/1969 | Stevens ........................ 128/2 |
| 3,612,058 A | 10/1971 | Ackerman ................. 128/348 |

(List continued on next page.)

FOREIGN PATENT DOCUMENTS

| EP | 0 277 366 A1 | 8/1988 |
| EP | 0 382 974 A1 | 8/1990 |
| EP | 0 473 045 A1 | 3/1992 |

(List continued on next page.)

OTHER PUBLICATIONS

Kolobow et al., "A New Thin–Walled Nonkinking Catheter for Peripheral Vascular Cannulation," *Surgery*, vol. 68, No. 4, Oct. 1970, pp. 625–626.

*Primary Examiner*—Max Hindenburg
(74) *Attorney, Agent, or Firm*—Crompton, Seager & Tufte, LLC

(57) ABSTRACT

A tubing assembly for manufacture for a catheter of the type having an inner tubular member defining a lumen, an outer tubular member surrounding said inner member, and a support member mounted between the tubular members to provide rigidity to the flexible catheter. The support member comprises a high tensile strength wire braid, and in the preferred embodiment comprises a stainless steel wire braid which has been tempered or hardened. This higher tensile strength affords significantly greater kink resistance to the flexible catheter. One wire braid has a tensile strength in the range of 300 to 425 kpsi and a braid density of approximately 40 pic. The high tensile strength wire braid has the disadvantage of tending to flare out at its free ends. Therefore, means are provided for preventing the flaring of the wire braid during manufacture of the tubing assembly. One means includes adhesive applied over the free ends. Another means includes a restraining sleeve applied over the free ends.

14 Claims, 4 Drawing Sheets

U.S. PATENT DOCUMENTS

| | | | | |
|---|---|---|---|---|
| 4,210,478 | A | 7/1980 | Shoney | 156/242 |
| 4,419,095 | A | 12/1983 | Nebergall et al. | 604/96 |
| 4,516,970 | A | 5/1985 | Kaufman et al. | 604/270 |
| 4,516,972 | A | 5/1985 | Samson | 604/282 |
| 4,531,943 | A | 7/1985 | Van Tassel et al. | 604/280 |
| 4,588,399 | A | 5/1986 | Nebergall et al. | 604/280 |
| 4,705,511 | A | 11/1987 | Kocak | 604/282 |
| 4,817,613 | A | 4/1989 | Jaraczewski et al. | 128/658 |
| 4,842,590 | A | 6/1989 | Tanabe et al. | 604/282 |
| 4,863,442 | A | 9/1989 | DeMello et al. | 604/282 |
| 4,898,591 | A | 2/1990 | Jang et al. | 604/282 |
| 4,981,478 | A | 1/1991 | Evard et al. | 604/282 |
| 5,017,259 | A | 5/1991 | Kohsai | 156/294 |
| 5,057,092 | A | 10/1991 | Webster, Jr. | |
| 5,069,674 | A | 12/1991 | Fearnot et al. | 604/282 |
| 5,078,702 | A | 1/1992 | Pomeranz | 604/280 |
| 5,160,559 | A | 11/1992 | Scovil et al. | 156/73.6 |
| 5,190,520 | A | 3/1993 | Fenton, Jr. et al. | 604/43 |
| 5,217,440 | A | 6/1993 | Frassica | 604/282 |
| 5,221,270 | A | 6/1993 | Parker | 604/282 |
| 5,221,372 | A | 6/1993 | Olson | 148/326 |
| 5,234,416 | A | 8/1993 | Macaulay | 604/282 |
| 5,254,107 | A | 10/1993 | Soltesz | 604/282 |
| 5,279,596 | A | 1/1994 | Castaneda et al. | 604/282 |
| 5,306,252 | A | 4/1994 | Yutori et al. | 604/164 |
| 5,335,305 | A | 8/1994 | Kosa et al. | 385/147 |
| 5,433,200 | A | 7/1995 | Fleischhacker | 128/657 |
| 5,603,705 | A | 2/1997 | Berg | 604/282 |
| 5,662,622 | A | 9/1997 | Gore et al. | 604/282 |
| 5,674,208 | A | 10/1997 | Berg et al. | 604/282 |
| 5,769,796 | A | 6/1998 | Palermo et al. | 600/585 |
| 5,911,715 | A | 6/1999 | Berg et al. | 604/525 |
| 5,951,495 | A | 9/1999 | Berg et al. | 600/585 |
| 5,954,651 | A | 9/1999 | Berg et al. | 600/434 |
| 6,212,422 | B1 | 4/2001 | Berg et al. | 600/435 |

FOREIGN PATENT DOCUMENTS

| | | |
|---|---|---|
| JP | 4-40652 | 4/1992 |
| JP | 5-84303 | 4/1993 |
| WO | WO 93/15785 | 8/1993 |
| WO | WO 96/20750 | 7/1996 |

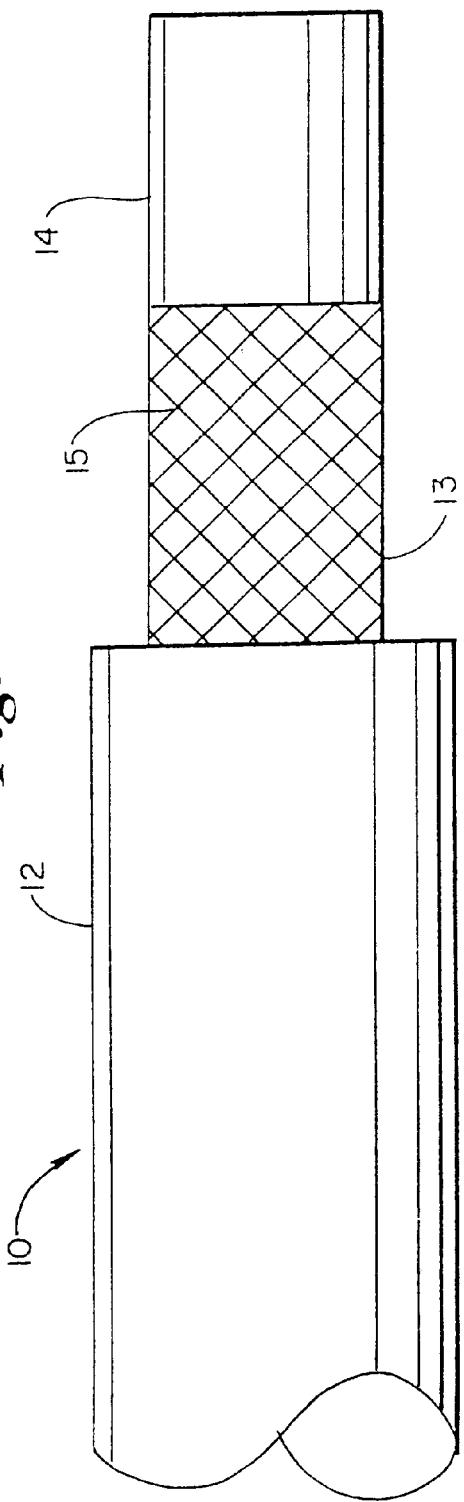
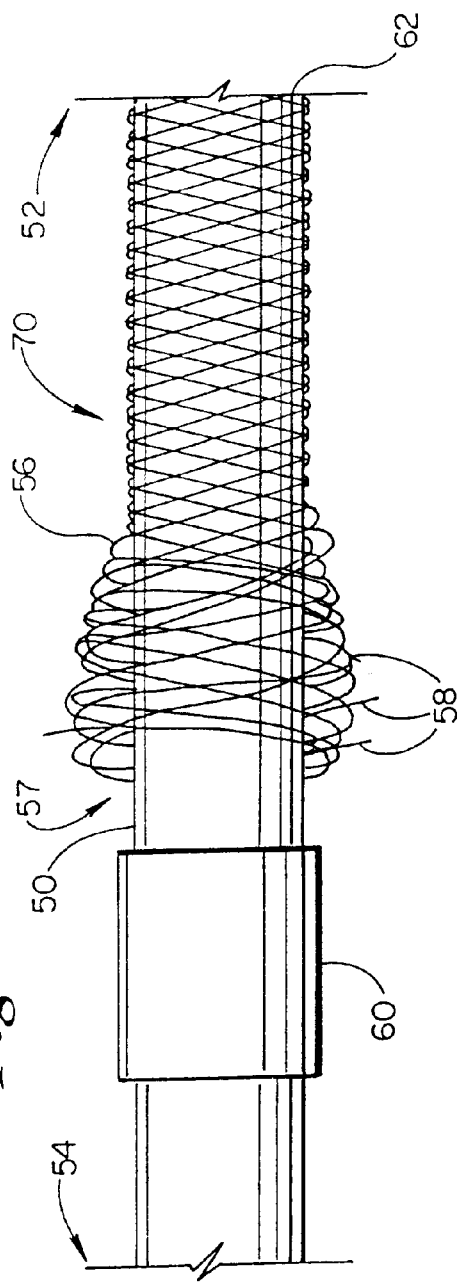

CATHETER HAVING A HIGH TENSILE STRENGTH BRAID WIRE CONSTRAINT AND METHOD OF MANUFACTURE

CROSS REFERENCE TO CO-PENDING APPLICATIONS

This application is a continuation of application Ser. No. 09/346,973, filed Jul. 2, 1999 now U.S. Pat. No. 6,212,422 which is a continuation of application Ser. No. 08/936,983, filed Sep. 25, 1997 now U.S. Pat. No. 5,954,651 which is a continuation-in-part of pending application Ser. No. 08/800,926, filed Feb. 13, 1997 now U.S. Pat. No. 5,951,495 which is a continuation-in-part of application Ser. No. 08/441,260, filed May 15, 1995, now U.S. Pat. No. 5,603,705, which is a continuation of application Ser. No. 08/171,925, filed Dec. 22, 1993, now abandoned. Application No. 09/875,367 this application is also a continuation-in-part of application Ser. No. 08/489,001, filed Jun. 8, 1995, now U.S. Pat. No. 5,674,208, which is a continuation of application Ser. No. 08/108,973, filed Aug. 18, 1993, now abandoned.

TECHNICAL FIELD

The present invention generally relates to the field of medical devices, and more particularly, to the field of catheters such as guide catheters used for the placement of medicines and medical devices within the body. Specifically, the invention is directed to a catheter tube, particularly useful in an intravascular guide catheter, incorporating a high tensile strength braid wire constraint.

BACKGROUND OF THE INVENTION

The use of intravascular catheters for treatment of the body is well known in the field of medicine. The need for a choice of catheter sizes and types has grown rapidly as the techniques for their use have been greatly improved and the types of medical uses have expanded quickly. One such catheter is a guide catheter which includes a tubular member having a lumen therethrough. Guide catheters are commonly used in diagnostic and treatment techniques related to vascular disease such as angioplasty. A guide catheter is inserted into the femoral artery and routed to a location near a treatment or diagnostic site through the aorta over the aortic arch to the ostium of a target vessel. The guide catheter provides a conduit so that fluid or another medical device can be delivered easily to the proximate location of treatment via the lumen of the guide catheter.

Prior art catheters often comprise a tubular member including a pair of congruent tubes, the inner one defining the lumen. A hub is connected at the proximal end of the tubes which in addition to providing access to the lumen for fluids and the like, is often used to provide torques and other necessary pressures to the tubes during their placement within the body. A tip of a selected design is placed at the distal end of the tubes. Flexibility is an essential part of the catheter so that it may be successfully torqued, pushed and pulled on its way through the vascular passage to the desired site in the body. For control of the catheter and to prevent its kinking from excessive flexing a certain amount of rigidity is also required. The prior art catheters often meet this need for rigidity by adding a support member between the two tubes. This support member may comprise a braid of metal wire wrapped around the inner tube, and often imbedded within the outer tube.

As specific examples of the type of prior art catheters described above, note U.S. Pat. No. 3,485,234, issued Dec. 23, 1969, to R. C. Stevens, for Tubular Products and Method of Making Same; and European Patent Application, Publication No. 0 277 366/A1, Priority Jun. 1, 1987, by Bruce H. Ward, for Guiding Catheter and Method for Making it. Each of these references teaches, in general, the prior art type of catheter discussed above.

One problem that has arisen is that as it becomes desirable to increase the diameter of the catheter lumen, it also becomes desirable to decrease the thickness of the walls of the tubes that form the catheter. However, it has been found that in thinner-walled catheters it is more difficult to prevent the kinking of the catheter. This negative effect on flexibility is overcome by the above cited co-pending application, Ser. No. 08/108,973, filed Aug. 18, 1993, entitled "Improved Thin-Walled Catheter" which is incorporated by reference herein. The disadvantage of the prior art was overcome by providing a high tensile, stainless steel braid as the support structure. However, it has been found that the use of the high tensile metal braid may cause an additional problem for practitioners of the catheter art. It has been seen that the high tensile wire has a tendency to flare or spring out in an area proximate the ends of the braid both before and during the heating process used in joining the catheter to a tip or other apparatus. In a similar way, this flaring and springing of the support braid wire is found in prior art catheters even when using the lower tensile type of wire. This flaring will interfere in the proper joinder of the catheter to, for example, a tip and is clearly undesirable and unacceptable in an intravenous catheter.

It is recognized that guide catheters preferably have a low friction inner lumen for improved passage of other catheter devices, such as an angioplasty catheter, through such lumen. Catheters incorporating a lumen lined with polytetrafluoroethylene (PTFE) to insure low friction are generally known. The soft atraumatic tip of prior art catheters, however, does not incorporate a polytetrafluoroethylene liner. Due to the softness of the tip material and the absence of the PTFE liner, the tip area can add significant friction opposition to advancing devices through the inner lumen of the catheter. Further, it is recognized that extending the braid wire into the atraumatic tip is not desirable, as this would significantly stiffen the tip area and counter its function of providing an atraumatic positioning of the distal end of the guide catheter. Thus, it is the clinical function of the tip that requires such tip to be very soft and free of wire braid. Terminating the braid prior to the soft tip increases the prevalence of problems associated with the flaring or springing out of the wire braid proximate its free ends near the distal tip.

Accordingly, the need exists for a catheter tube construction incorporating a lubricous liner and overlying wire braid structure, wherein the free ends of the wire braid proximate the location of attachment of a soft atraumatic tip are prevented from flaring out during manufacture of the catheter tube. Further, a need exists for an atraumatic tip design which incorporates a lubricous liner to reduce the friction caused by the soft tip material when passing devices through the lumen of the tip. The present invention addresses these needs, as well as other problems associated with existing guide catheter tube and tip designs. The present invention also offers further advantages over the prior art and solves other problems associated therewith.

SUMMARY OF THE INVENTION

The present invention overcomes the above-identified disadvantages by providing an improved catheter tube incorporating a lubricous liner in combination with a wire braid overlying the lubricous liner, wherein the free ends of the wire braid are effectively restrained to overcome the inherent spring property of the material and prevent protrusion of the free ends proximal to the soft tip when assembled.

The present invention further provides a catheter tube incorporating a lubricous liner, preferably polytetrafluoroethylene, which extends at least through a portion of the inner lumen of the atraumatic tip to reduce friction therethrough. In a preferred embodiment, the liner extends through essentially the entire length of the inner lumen of the soft atraumatic tip.

The present invention further includes improved methods for joinder of the catheter to any selected apparatus, such as joinder of the tip to the catheter tube.

Two overall embodiments and methods of manufacturing these embodiments are disclosed herein. In a first embodiment, a lap-type joint is formed at the distal end of a section of catheter shaft subsequent to manufacture of a tubular member having an inner tube, an outer congruent tube and a wire braid therebetween. A means for restraining the free ends of the wire braid in the lap joint area is provided with subsequent addition of the atraumatic tip, a portion of which overlies the restrained free ends of the wire braid.

In a second embodiment, a braided shaft region and a non-braided tip region are formed over a continuous liner or inner tube, preferably a polytetrafluoroethylene liner or inner tube. This is achieved by sleeving a preformed segment of wire braid over a preformed inner tubular member or a liner. A molding sleeve is then tracked over the braid and inner tubular member which pulls the braid down tightly to the inner tubular member, including the flaring -ends of the wire braid. With the molding sleeve in place, adhesive material is applied via capillary action to the region having the molding sleeve restraining the ends of the wire braid, which when cured hold the ends in place upon removal of the molding sleeve. This design further allows the inner tubular member to extend braid-free through a tip attached proximate the end of the wire braid.

In the preferred embodiment at least one end of the catheter, normally the distal end, is ground down by an abrasion tool to provide a length of reduced diameter suitable, in particular, for lap-joint type connection to a tip or other apparatus. A restraining material, preferably a thin-walled heat shrink polyester, is also provided to be placed over at least a portion of the reduced diameter length to prevent flaring of the metal braid during the joinder process.

In this embodiment, the restraining material can be in the form of a sleeve having a tubular shape with an inner diameter adapted to allow placement of the sleeve over at least a portion of the reduced diameter length at the end of the catheter; and a length at most equal to the length of the reduced diameter portion of the catheter.

As described, the apparatus and method of this embodiment provides the advantage of allowing use of the high tensile metal braid by restraining flaring of the metal during heat bonding to a tip or other device, thus improving kink performance in the thin-walled catheters which use the high tensile wire. The embodiment provides the same restraining advantage for catheters which may not use the high tensile wire, but which have the same flaring problem. This embodiment also provides the advantage of providing a more durable bond of the catheter to the tip or other apparatus by the increased surface area of the lap type bonding. Finally, the apparatus of this embodiment offers an additional advantage in the form of a stiffness transition in that the ground or abraded step portion of the bond balances the hardness of the main catheter to the softness of a tip, a balance which is known to provide clinical value.

In the second embodiment of the present invention, a catheter shaft construction is provided that incorporates adhesive means for preventing the free ends of a braid member from flaring outward during assembly. Further, this embodiment also provides a continuous inner tubular member or liner that is preferably lubricous, such as polytetrafluoroethylene, which extends through the tip portion of the catheter tubular member, yet has a portion which is free of the braid member. With the inner liner extending through the catheter shaft and tip, the braid or braid wire ends uniformly just proximal to the beginning of the distal soft tip, which results in the above-identified flaring of the braid wire. Thus, a preferred method has been developed to restrain the flaring braid wires during assembly of the catheter shaft which provides for a continuous liner for both the shaft and tip regions and a braid-free tip section. The method does not require braid removal and does not add wall thickness to restrain the flared ends.

With this second preferred embodiment, a first step in the method of manufacture is to form a braided shaft region and a non-braided tip region over a continuous liner. This is preferably achieved by sleeving the braid or wire braid over a section of liner which is placed over a core or mandrel. The distal end of the braid terminates proximal to the distal end of the liner to separate the shaft and tip regions.

A molding sleeve is then tracked over the braid and liner. The molding sleeve is preferably a tubular member having a lumen therethrough which, when tracked over the braid, pulls the braid wire down tightly to conform to the outer longitudinal surface of the liner. At the end of the wire braid, the advancing molding sleeve forces the free braid ends to conform back into the original braid pattern and into the lumen of the molding sleeve. Once the distal ends of the braid member have been conformed by the molding sleeve, adhesive means is injected into the cavity between the molding sleeve and the liner over a portion of the braid proximate its distal end. Preferably a high temperature (350–400° F.), soft (25D–50D) restraining seal in liquid form is injected into the cavity. Capillary action is recognized as facilitating this process by sucking the liquid seal restraining material from outside the molding sleeve to inside.

The liquid seal is then cured through the molding sleeve. A preferred adhesive means is an ultraviolet light (UV) curable adhesive which is used in conjunction with a clear molding sleeve that allows UV light to pass through the clear molding sleeve walls which cures the adhesive. Although other adhesives and curing methods and appropriate adhesives are recognized as within the scope of the invention, including such methods as heat, catalyst and moisture.

Upon removing the molding sleeve, the resulting intermediate assembly or tubular assembly includes a micro-thin band molded from the adhesive means or liquid seal that circumferentially encapsulates the distal free wire ends. The restraining band preferably adheres to the liner and encapsulates the wire braid. The band is very thin, uniform in thickness, and concentric, due to the forming of the liquid seal within the molding sleeve. The wire braid ends are uniformly and distinctly ended while the inner tubular member or liner continues distally to provide a braid-free region for tip attachment.

An outer tubular member overlies the intermediate tube assembly over at least a portion of the assembly having the braid thereon. A tip member overlies the portion of the liner which extends distally beyond the braid. The distal end of the tip member can extend beyond the distal end of the liner, but in preferred embodiments, the tip-member is co-extensive with the liner to provide an atraumatic tip having a continuous liner therethrough.

These and other various advantages and features of novelty which characterize the present invention are pointed out with particularity in the claims annexed hereto and forming a part hereof. However, for a better understanding of the invention, its advantages and the objects obtained by its use, reference should be made to the drawings which form a further part hereof and to the accompanying descriptive matter, in which there are illustrated and described preferred embodiments of the present invention.

The present invention overcomes the disadvantages found in the prior art by providing an improved metallic support member that has a greater tensile strength and a greater Modulus of Elasticity than non-metallic support materials and therefore can offer an increase in the rigidity required to prevent kinking without sacrificing the needed flexibility. The increased tensile strength of the present invention is primarily achieved through the tempering or hardening of the metal used for the support member. In the prior art, the support member, such as a stainless steel braid, was annealed, thus resulting in a comparatively low tensile strength.

In the preferred embodiment of this invention the support member comprises a braid made of tempered stainless steel wires. A fully hardened metal wire is preferred, such as #304 stainless steel which will yield a tensile strength in the range of 300 to 475 kilopounds per square inch (kpsi) and which has a Modulus of elasticity ranging from 28,000,000 psi fully hardened to 26,000,000 not fully hardened. Other types of stainless steel can be used, including those having lower tensile strength. It has been found that tensile strengths as low as 200 kpsi offer advantageous kink performance.

Also, in the preferred embodiment of this invention, the preferred diameter of the braiding wire has been found to be 0.002 inches. However, it should also be noted that other diameters can be successfully utilized, such as in the range of 0.00075 to 0.0035 inches, dependent on the dimensions of the catheter thin wall.

In the preferred embodiment of this invention it has further been found that the preferred braid construction is 16 strands of tubular braid, with a braid density of 40 crosses per inch (pic). Other combinations of braid strands and pic densities have also been found to be useful.

BRIEF DESCRIPTION OF THE INVENTION

In the drawings, in which like reference numerals indicate corresponding parts or elements of preferred embodiments of the present invention throughout the several views:

FIG. 3 is a plan view of FIG. 2 showing the sleeve after mounting on the ground-down length of the catheter;

FIG. 4 is a plan view of a liner or inner tubular member having a braid member inserted thereover illustrating the flared free ends of the braid;

DETAILED DESCRIPTION OF PREFERRED EMBODIMENTS

Figure 1:
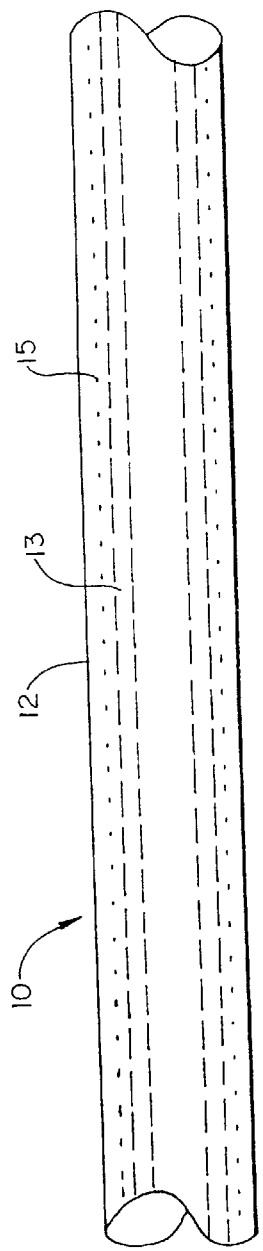
FIG. 1 is a plan view showing a portion of a catheter.
Figure 2:
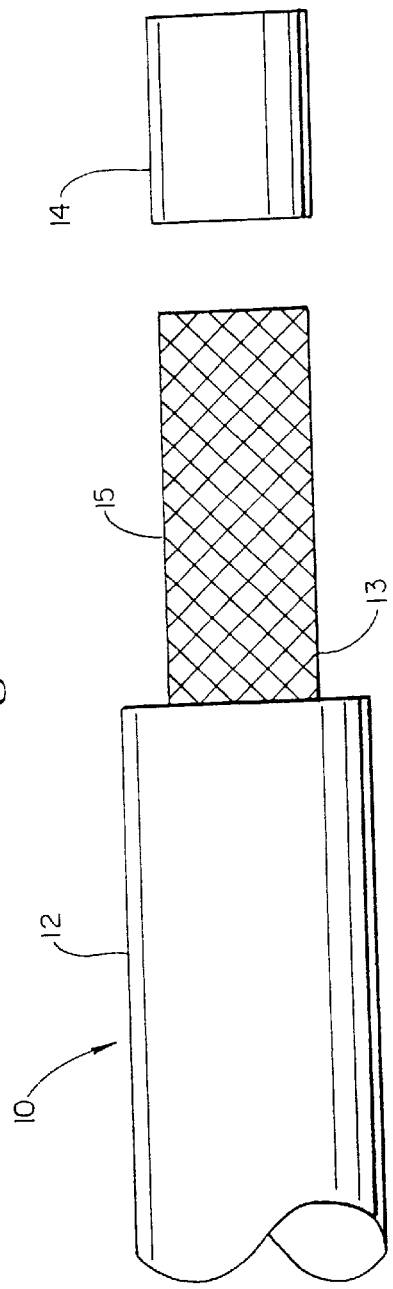
FIG. 2 is another plan view of a portion of the catheter of FIG. 1 with a length of the catheter ground down to a lesser diameter, and showing a sleeve.

As required, detailed embodiments of the present invention are disclosed herein. However, it should be understood that the disclosed embodiments are merely exemplary of the present invention which may be embodied in various systems. Thus, the discussion with respect to FIGS. 1–3 are directed to a first embodiment of the present invention, while the discussion with respect to FIGS. 4–8 are directed to a second embodiment. It is, however, recognized that elements of each embodiment may be incorporated in a catheter tube construction in combinations as would be well understood by one skilled in the art. Therefore, specific details disclosed herein are not to be interpreted as limiting, but rather as a basis for the claims and as a representative basis for teaching one skilled in the art to variously practice the present invention.

FIG. 1 shows a guide catheter 10, which may be a thin-walled catheter. Catheter 10 comprises an outer tubular member 12 which surrounds and is coaxial with an inner tubular member 13 shown in dashed phantom lines. A support member 15 is shown in dotted phantom lines. Member 15 is a braid of metal wire, which may be high tensile wire, that also surrounds and is coaxial with member 13.

FIG. 2 is a drawing of a portion of catheter 10. Member 12 is shown having an end portion ground or abraded away. As shown in FIG. 2, member 12 has been completely ground down to metal braid 15. However, it should be recognized that this invention will also operate fully if only a portion of member 12 is abraded away. FIG. 2 also shows a restraining device 14. Device 14 is shown in a first preferred embodiment to be a tubular sleeve. Sleeve 14 is, preferably, a thin-walled heat shrink polyester having a length sized to cover at least a portion of the abraded length of member 12, and an inner diameter sized to allow it to fit over the reduced diameter of the end portion of catheter 10 caused by the abrasion of member 12. In this preferred embodiment, sleeve 14 has a thickness of approximately 0.0005 inches, thus allowing it to be completely imbedded between the reduced diameter portion of catheter 10 and the tip or other device used to complete the lap joint with catheter 10.

FIG. 3 is a plan view of the apparatus of FIG. 2 showing the restraining device 14 mounted on the reduced diameter portion of catheter 10. Due to the proper sizing of device or sleeve 14, it has been slid onto and covers at least a portion of the reduced diameter region of catheter 10. Sleeve 14 is seen to fit over enough of the end portion of braid 15 so that, when sleeve 14 is heated, it will shrink to and retain the metal wire strands of braid 15.

It should be recognized that though restraining device 14 is shown and described as a tubular member in this embodiment, other forms could be used as well. For example, device 14 could be a simple strip of heat shrink polyester adapted to be wrapped around the reduced diameter portion of catheter 10. The important feature is that after it has been heated to encapsulate the end of the wire braid, device 14 restrains the wire from surfacing through any joinder by flaring or springing out.

For the process of forming the apparatus of this invention, an abrasive forming tool is used to remove the material of member 12 from its outside surface for 360 degrees from one end of catheter 10. This forms a straight step from the end which allows the abraded or ground portion of catheter 10 to act as the male portion of a lap joint to coact with a female portion of a soft tip or other device it is desired to connect to the apparatus of this invention. The step is preferably a reduction in wall thickness of approximately 0.002 to 0.006 inches, thus allowing for the use of the 0.0005 inch restraining device 14. The length of the abraded portion of catheter 10 is preferably about 0.125 inches, thus allowing for a significant bonding surface area when used in a lap joint. As used herein, the terms "ground" and "abraded" have the same meaning.

Figure 6:
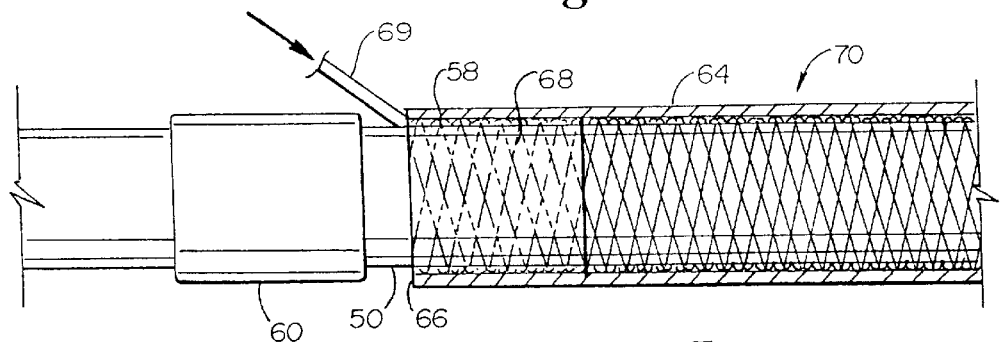
FIG. 6 is a partial cross-sectional view illustrating addition of adhesive means to the distal portion of the assembly between the liner and molding sleeve.
Figure 7:
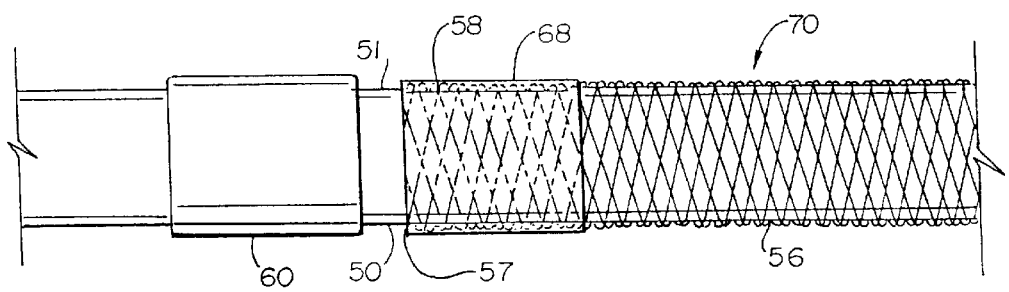
FIG. 7 is a plan view illustrating the restrained braid ends upon curing of the adhesive means and removal of the molding sleeve.
Figure 8:
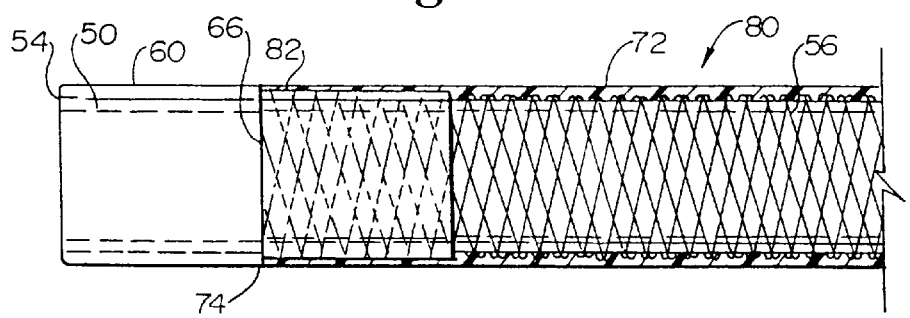
FIG. 8 depicts a partial cross-section of a distal portion of a catheter shaft of the embodiment of FIG. 7 with an outer tubular member overlying the braid assembly and a tip portion overlying the liner distal of the braid assembly.

Now referring to FIGS. 4–8, a series of illustrations are provided to depict and describe another preferred embodiment of the catheter tubular assembly of the present invention and a method of manufacturing such tubular assembly. The method of manufacture of the final tubular assembly depicted in FIG. 7 and the catheter assembly depicted in FIG. 8 is first described for a better understanding of the final apparatus.

Referring now to FIG. 4, a tubular member 50 is first provided for manufacture of a tubular assembly 70 of the present invention. The tubular member 50 preferably has a lumen 62 therethrough. However, during manufacture of the tubular assembly, a mandrel or core is inserted in the lumen 62 to prevent collapse of the tubular member 50. The mandrel can include a stainless steel wire or a polymeric rod.

The tubular member 50 is preferably manufactured from a lubricous polymeric material. A preferred material of construction is polytetrafluoroethylene (PTFE). In the preferred method of manufacture, the tubular member 50 is cut to a discrete length slightly in excess of the length of a desired finished product. A braided wire tubular member 56 overlies a portion of the outside longitudinal surface 51 over a portion of the length of the tubular member 50. The braid 56 is preferably manufactured from metallic wire. A preferred material of construction is stainless steel, more preferably a high tensile stainless steel wire. In a preferred method of manufacture, the braid 56 is preformed into a braided wire tubular member 56 of required length which is sleeved over the tubular member 50.

As depicted in FIG. 4, the braid 56 has a distal end shown generally at 57. The distal end 57 flares outward due to the inherent spring property of the stainless steel material which is utilized in a preferred embodiment. The distal free ends 58 pose problems in assembly of catheter tubing as described previously.

Also depicted in FIG. 4 is a tip member 60 which has been preloaded onto the tubular member 50 by sliding the tip member over the distal end 54 of the tubular member 50. The final assembly of the tip member 60 to the catheter shaft will be described later in conjunction with FIGS. 7 and 8.

Figure 5:
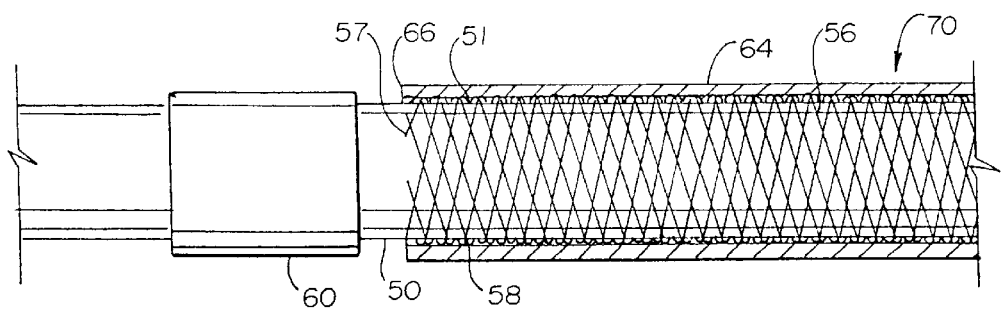
FIG. 5 is a partial cross-sectional view of the assembly of FIG. 4 having a molding sleeve inserted thereover to conform the wire braid.

Now referring to FIG. 5, the assembly of FIG. 4 is depicted having a molding sleeve 64 disposed thereover. The molding sleeve has a distal end 66 and a proximal end 67 (not shown). As depicted in FIG. 5, the molding sleeve 64 includes a tubular portion having a lumen therethrough. The molding sleeve 64 is tracked over the tubular member 50 and braid 56 so that the braid 56, including the free ends 58, are caused to conform to the outside longitudinal surface 51 of the tubular member 50. FIG. 5 depicts a preferred embodiment, wherein the distal end 66 of the molding sleeve 64 terminates proximate the distal end 57 of the braid 56.

With the molding sleeve 64 positioned as depicted in FIG. 5, now referring to FIG. 6, adhesive means 68 is applied to the tubular member 50 proximate the restrained free ends 58 under the molding sleeve 64 to prevent flaring of the free ends 58 upon removal of the molding sleeve 64. In preferred embodiments, the adhesive means 58 is simply applied by depositing a bead of adhesive through a syringe or other applicator 69 around the circumference of the tubular member 50 at the distal end 66 of the molding sleeve 64. Capillary action assists in drawing the adhesive means 58 under the distal end 66 of the molding sleeve 64 between the tubular member 50, longitudinal surface 51 and molding sleeve 64.

In preferred embodiments, the adhesive means 58 is an ultraviolet light curable adhesive. These adhesives can include: polyurethanes, epoxies, acrylics and mixtures thereof. However, it is recognized that other adhesives which are heat curable, catalyst curable or moisture curable can be utilized. These other adhesives can include: cyanoacrylates, epoxies, hot melt adhesives, acrylics, silicones and mixtures thereof.

Upon application of the adhesive means 68, the adhesive means 68 is cured while the molding sleeve 64 remains in place. In a preferred embodiment, wherein the adhesive means 68 is ultraviolet light curable, the molding sleeve 64 must allow passage of ultraviolet light through the walls thereof. Therefore, the molding sleeve is preferably clear. The clear molding sleeve 64 also allows visualization of the braid 56 as it is conformed to the tubular member 50.

Now referring to FIG. 7, the finished tubular assembly 70 or intermediate assembly 70 for use in manufacturing a catheter is illustrated. As shown, upon curing of the adhesive means 68, the molding sleeve 64 is removed and the adhesive means 68 restrains the free ends 58 of the braid 56.

As depicted in FIG. 7, the thickness of the adhesive means 68 is grossly exaggerated so that it is visible. In preferred embodiments, the adhesive means 68 provides a uniform, micro-thin seal which is molded circumferentially around the distal braid ends 58. The thickness of the adhesive means 68 does not interfere with subsequent processing of the tubular assembly 70.

Thus, the tubular assembly 70 of the present invention includes a tubular member 50 having a proximal end, a distal end and an outer longitudinal surface 51. The braid member 56 overlies the tubular member 50 and conforms to the outer longitudinal surface 51. The braid 56 has a distal end 57 which includes a plurality of free ends or terminal ends 58. A sufficient quantify of adhesive means 68 restrains the plurality of terminal ends 58 of the braid member 56 to maintain conformance of the plurality of terminal ends 58 to the longitudinal surface 51 of the tubular member 50.

The tubular assembly of FIG. 7 is preferably incorporated into a catheter assembly 80 as depicted in FIG. 8. As depicted in FIG. 8, an outer tubular member 72 overlies the braid member 56 and has a distal end 82 terminating proximate the distal end 66 of the braid member 56. The outer tubular member 72, however, terminates proximal of the distal end 54 of the inner tubular member 50.

The tip member 60, previously disclosed, includes at least a portion of the tip member 60 overlying the inner tubular member 50 outer longitudinal surface 51 distal of the distal end 66 of the braid member 56. As depicted in FIG. 8, the proximal end 74 of the tip member 60 is in contact with the distal end 82 of the outer tubular member 72. As depicted in a preferred embodiment, the inner tubular member 50 distal of the braid member 56 is co-extensive with the tip member and forms a braidless tip portion of the catheter assembly 80 having a continuous inner tubular member therethrough.

It is recognized that the outer tubular member 72 may be added in any way known in the art. This can include extruding a material over the tubular assembly 70. In a preferred method of manufacture, a plurality of tubular segments are slidably received over the tubular assembly 70 along with the tip member 60. The tubular members, including the tip member 60, are abutted to each other and a heat shrink polymer sleeve is placed over the entire assembly. The assembly is then heated or baked to fuse the assembly with subsequent removal of the polymer sleeve. This preferred method of manufacture is disclosed in detail in co-pending, commonly assigned, application Ser. No. 08/800,927, filed on Feb. 13, 1997, entitled "Guide Catheter Having Selected Flexural Modulus Segments", the disclosure of which is incorporated herein by reference.

One major reason kinking increases with thin-walled catheters is that the rigidity provided by the prior art metallic support members becomes insufficient as the catheter walls become thinner. Such prior art support members are often constructed of a braid made from annealed stainless steel wire. It is well known that the annealing process will yield a comparatively low tensile strength, for example, about 140 kpsi.

Catheter failure due to kinking is caused by compressive forces that collapse the catheter wall into its lumen. The support member, or braiding wire, is used to resist the compressive force. As the catheter is put through the placement process to reach the desired placement within the body it is torqued and maneuvered such that it is forced into tighter loops and bends. As these loops and bends become tighter and tighter, the compressive forces increase until the yield strength of the support member is exceeded. When the external stress (compressive forces) exceeds the ultimate tensile strength (stress) of the braiding wire material, failure or kinking of the catheter wall occurs.

From the above definition of the failure mechanism for kinking, it becomes apparent that an increase in the tensile strength of the wire will allow higher compressive forces to be applied to the catheter wall without failure. Thus the higher tolerance for stress before failure correlates directly to thinner catheter walls and tighter bends than possible with annealed or lower tensile strength wire.

The apparatus of this invention overcomes the above kinking problem by using a tempered or hardened metal for support member 15. In the preferred embodiment member 15 is a braid using no. 304 stainless steel wire which has been hardened to have a high tensile strength in the range of 300 to 475 kpsi. Study has shown that tensile strengths down to 200 kpsi also offer advantageous kink resistance over the annealed braid.

The following chart illustrates the typical lumen sizes obtainable for various catheter french sizes, based on the tensile strength of the support braid wire:

| FRENCH SIZE | ANNEALED BRAID - I.D. | HIGH TENSILE BRAID - I.D. |
| --- | --- | --- |
| 6F | 0.060 inches | 0.066 inches |
| 7F | 0.072 inches | 0.076 inches |
| 8F | 0.080 inches | 0.086 inches |
| 9F | 0.092 inches | 0.098 inches |

From the above chart the advantage of the tempered or high tensile strength braid can be clearly seen. In all french sizes shown, the high tensile braid allows a larger lumen (thinner wall) than does the prior art or annealed braid.

Figure 9:
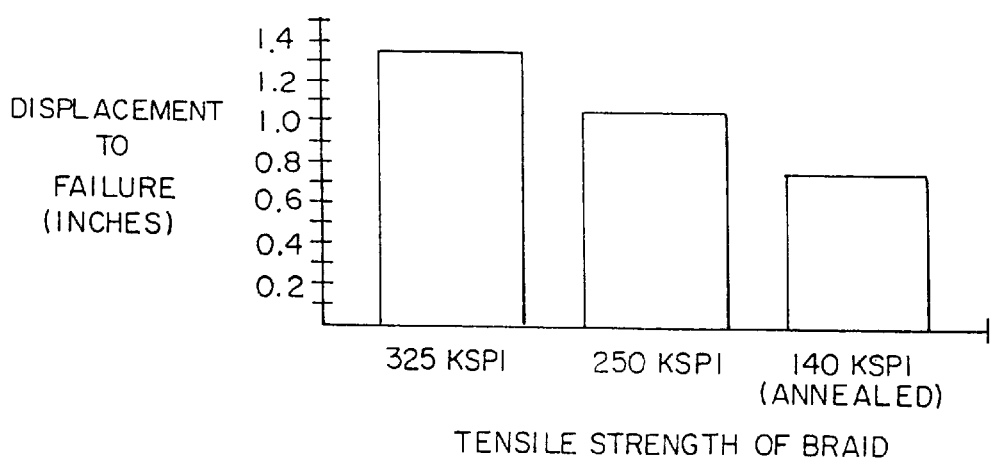
FIG. 9 is a bar graph depicting catheter kink resistance at various tensile strengths of the support braid of the catheter of this invention.

Reference is made to FIG. 9 where the bar graph also clearly depicts the advantage of the present invention with regard to kink performance. Here it can clearly be seen that the preferred embodiment of the present invention (325 kpsi braid wire) offers far greater kink performance or displacement-to-failure than does the prior art annealed version (140 kpsi braid wire). It can also be seen that an even lower tempered tensile strength of 250 kpsi braid wire still offers significantly improved kink performance over the annealed braid wire.

Finally, it has also been found that certain braid construction features are preferred for this invention. The preferred diameter of the braid wire is 0.002 inches, though diameters in the range of 0.00075 to 0.0035 are also acceptable dependent on the catheter wall dimensions. One embodiment has a braiding density of at least 10 pic. The preferred braiding density is 40 pic, though other pic densities have also been found to be advantageous.

Having thus described the preferred embodiments of the present invention, those of skill in the art will readily appreciate the other useful embodiments within the scope of the attached claims.

What is claimed is:

1. A method of forming a tubular assembly for use in a catheter comprising the steps of:
   providing a tubular member having a distal end and a proximal end with a braid overlying a portion of the length of said tubular member, said braid having a distal end including free ends proximate the distal end of said tubular member;
   providing a molding sleeve having a proximal end and a distal end, said molding sleeve including a tubular portion having a lumen therethrough;
   tracking said molding sleeve over said tubular member and said braid so that said braid, including said free ends, conforms to the tubular member; and
   applying adhesive means to said tubular member proximate said restrained free ends under said molding sleeve to prevent flaring of said free ends upon removal of said molding sleeve.

2. The method of claim 1, wherein said distal end of said molding sleeve terminates proximate said distal end of said braid when tracked over said tubular member and said braid.

3. The method of claim 2, wherein said adhesive means is applied around a circumference of said distal end of said molding sleeve so that said adhesive means flows under said molding sleeve by capillary action.

4. The method of claim 1, further comprising the steps of curing said adhesive means and removing said molding sleeve.

5. The method of claim 4, wherein said molding sleeve passes ultraviolet light through the wall thereof and said curing includes application of ultraviolet light to said adhesive means.

6. A method of forming a tubular assembly for use in a catheter comprising the steps of:

provide a tubular member having a distal end and a proximal end with a braid overlying an outer surface of a portion of the length of said tubular member, said braid having a distal end with free ends proximate the distal end of said tubular member;

providing means for restraining said free ends in conformance with said outer surface of said tubular member; and conforming said free ends to said outer surface with said means for restraining said free ends.

7. The method of claim 6, wherein said means for restraining is an adhesive.

8. The method of claim 7, wherein said adhesive is applied around a circumference of said distal end of said braid having free ends.

9. The method of claim 6, wherein said means for restraining is a polymeric sleeve.

10. The method of claim 9, wherein said polymeric sleeve is heat shrinkable.

11. A method for manufacturing a catheter tube comprising the steps of: providing a first tubular member having a distal end and a proximal end;

providing a braided wire tubular member having a proximal end, a distal end and a lumen therethrough;

sleeving said braided wire tubular member over said first tubular member, said distal end of said braided wire tubular member terminating a distance proximal of said distal end of said first tubular member, said braided wire tubular member having free ends at the distal end thereof;

providing a molding sleeve having a proximal end and a distal end, said molding sleeve including a tubular portion having a lumen therethrough;

tracking said molding sleeve over said first tubular member and said braided wire tubular member so that said braided wire tubular member, including said free ends, conforms to said first tubular member, said distal end of said molding sleeve positioned to terminate proximate said distal end of said braided wire tubular member;

applying adhesive means to said tubular member proximate said restrained free ends under said molding sleeve to prevent flaring of said free ends;

curing said adhesive means;

removing said molding sleeve;

overlaying said first tubular member in the region having said braided wire tubular member thereon with at least one segment of a second tubular member; and overlaying at least a portion of said first tubular member distal of said distal end of said braided wire tubular member with a tip member.

12. The method of claim 11, wherein said distal end of said molding sleeve terminates proximate said distal end of said braid when tracked over said tubular member and said braid.

13. The method of claim 12, wherein said adhesive means is applied around a circumference of said distal end of said molding sleeve so that said adhesive means flows under said molding sleeve by capillary action.

14. The method of claim 13, wherein said molding sleeve passes ultraviolet light through the wall thereof and said curing includes application of ultraviolet light to said adhesive means.

* * * * *

UNITED STATES PATENT AND TRADEMARK OFFICE
CERTIFICATE OF CORRECTION

PATENT NO. : 6,505,066 B2
DATED : January 7, 2003
INVENTOR(S) : Todd A. Berg et al.

It is certified that error appears in the above-identified patent and that said Letters Patent is hereby corrected as shown below:

<u>Column 12,</u>
Line 31, delete "claim 13" and insert therefor -- claim 11 --.

Signed and Sealed this

Twenty-ninth Day of July, 2003

JAMES E. ROGAN
*Director of the United States Patent and Trademark Office*